United States Patent [19]

Akers, Jr.

[11] 4,331,923
[45] May 25, 1982

[54] SALTS MONITORING DEVICE

[76] Inventor: Raymond F. Akers, Jr., 202 Summit Ave., Mantua, N.J. 08051

[21] Appl. No.: 64,268

[22] Filed: Aug. 6, 1979

[51] Int. Cl.³ .............................................. G01N 27/42
[52] U.S. Cl. ................................. 324/449; 324/446; 324/442
[58] Field of Search ............... 324/441, 442, 446, 449, 324/76 A, 78 J; 204/195 R

[56] References Cited

U.S. PATENT DOCUMENTS

| | | | |
|---|---|---|---|
| 3,000,805 | 9/1961 | Carriti et al. | 204/195 |
| 3,004,214 | 10/1961 | Wells | 324/30 |
| 3,061,773 | 10/1962 | Ellison et al. | 324/30 |
| 3,161,823 | 12/1964 | Uithoven | 324/29 |
| 3,250,689 | 5/1966 | Seyl | 204/1 |
| 3,258,682 | 6/1966 | Maurer | 324/30 |
| 3,774,104 | 11/1973 | Andersen | 324/30 B |
| 3,781,660 | 12/1973 | Ludt | 324/30 R |
| 3,922,598 | 11/1975 | Steuer | 324/30 R |
| 3,936,735 | 2/1976 | de Bough | 324/57 R |
| 3,980,944 | 9/1976 | Gallant et al. | 324/442 |
| 3,992,662 | 11/1976 | Koepnick et al. | 324/442 |
| 4,028,618 | 6/1977 | Teass, Jr. | 324/30 R |
| 4,074,027 | 2/1978 | Akers | 429/10 |

*Primary Examiner*—David K. Moore

[57] ABSTRACT

Circuitry is disclosed for measuring the quantity of total dissolved ionized salts in an undiluted aqueous sample. A bi-level power supply operating through a square wave generator and voltage follower creates a low amplitude AC signal at a predetermined level above a ground reference. The control voltage is applied through a conductivity probe assembly to two series connected operational amplifiers operating through a bridge assembly and meter movement to provide a reading of the total dissolved ionized salts in the sample as a function of their ionization characteristics.

5 Claims, 3 Drawing Figures

SALTS MONITORING DEVICE

BACKGROUND OF THE INVENTION

The present invention relates to equipment for monitoring the quantity of total dissolved ionized salts in an undiluted sample and, more specifically, to apparatus for measuring the salt content of body urine.

Medical research and laboratory studies definitely show a definable relationship between excess body salts and conditions of overweightness, heart attack and cardiovascular disease. These various body salts are derived from minerals that are ingested in food and water which is eaten and drank. Certain amounts of salts are required to allow for proper body chemistry and function. However, excess salts in the body present a potentially hazardous health condition.

As food and water intake is processed through the body and enters the bloodstream, the reflection of the blood condition is found in the body urine. Urine reveals daily what has been eaten and drank that day and monitoring of a urine sample is one of the significant body functions which may be monitored to determine body salt concentration and thus, the existence of hazardous body-salt conditions.

A common characteristic of all salts is that they form electrolytes due to their ionization characteristics when dissolved in water of which urine is principally composed of. An electrolyte affects the conductivity of water depending upon the ionization characteristics of the particular electrolyte and the quantity of the electrolyte present. Thus, the measure of conductivity of a urine sample is a measure of the electrolytic properties of the sample which, in turn, is a function of the ionization characteristics of the sample as a result of the total dissolved ionized salts in the sample derived from the body.

The concentration or strength of the body salts in the blood and consequently in the urine forming the electrolyte can be measured electronically. The unit of this measurement is called a "Micromho" and is a unit of conductivity. The higher the reading the greater the conductivity and thus, the greater the strength of electrolyte or salt content in the sample.

Medical studies show that the Micromho reading of a normal urine sample should be in the 12,000 range. A reading of 24,000 Micromhos is considered to be in the danger area and at a salt level which is excessive and potentially dangerous to the person.

There are commercially available today meters which measure the salt content of urine. Such meters as heretofore known utilize extremely complex means for generating reference voltages and multiple and further complex stages of amplification to arrive at an electronic signal indicative of the conductivity of the sample and thus, the salt content of the urine. Such meters as these are very complex and delicate in their adjustment and maintenance whereby their use requires a skilled technician. Additionally, their cost is extremely high and generally beyond that which can be afforded by the average user. Further, such prior art devices require the urine to be diluted and the probes platinum plated and wear out quickly.

SUMMARY OF THE INVENTION

It is the object of the present invention to provide an efficient, reliable and economic salts monitoring device which provides a reading of the total quantity of dissolved ionized salts within an undiluted sample to provide monitoring of the salt concentration within the body.

Another object is to provide a simple inexpensive portable device for use in the home by unskilled persons to monitor salt concentration in undiluted urine.

The salts monitoring apparatus of the present invention achieves the foregoing object. In accordance with the present invention, a bi-level power supply is provided in which the first voltage level is relatively large in magnitude in comparison to the second voltage level with reference to ground.

A reference voltage for the system is created by means of a square wave oscillator circuit operating between the first and second voltage levels which provides an output to a voltage divider. The relative impedance of the voltage divider is set such that the output at the midpoint of the voltage divider provides a square wave signal of significantly reduced amplitude slightly above the second voltage level which provides the input to an operational amplifier connected in a voltage follower configuration to provide a final reference output voltage signal of low impedance but at a predetermined level above ground.

The final reference voltage output for the system provides the input to a conductivity probe assembly which is adapted to be submerged into the sample to be monitored. The probe assembly provides the input to two series connected operational amplifiers whose final output is therefore a function of the conductivity of the sample being monitored and thus, a function of the quantity of total dissolved salts in the sample.

A temperature compensating device is placed in circuit with one of the probe assemblies and the feedback loop of the first operational amplifier. The slope and direction of the temperature compensating device is such that the feedback to the operational amplifier will be adjusted to linearly compensate for temperature variation of the sample being tested.

The output of the second operational amplifier is provided as the input to a full wave bridge. The output of the full wave bridge is, in turn, applied to a high impedance meter movement which is calibrated to provide a direct reading of conductivity of the sample being monitored and to thus give a reading of the total dissolved ionized salts in the urine sample being tested.

Other objects and advantages of the present invention will become apparent from the detailed description thereof which follows taken in conjunction with the drawings.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 1:
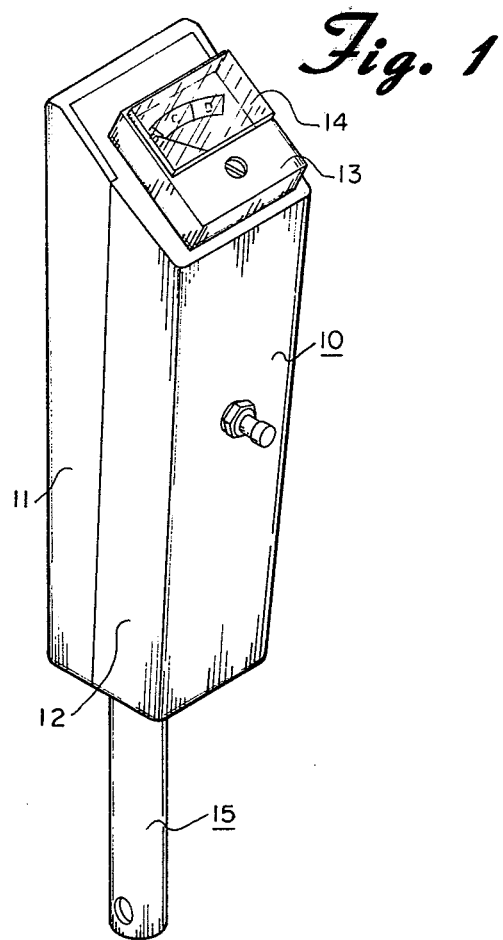
FIG. 1 is a perspective view of the salts monitoring device of the present invention including the housing therefor.
Figure 2:
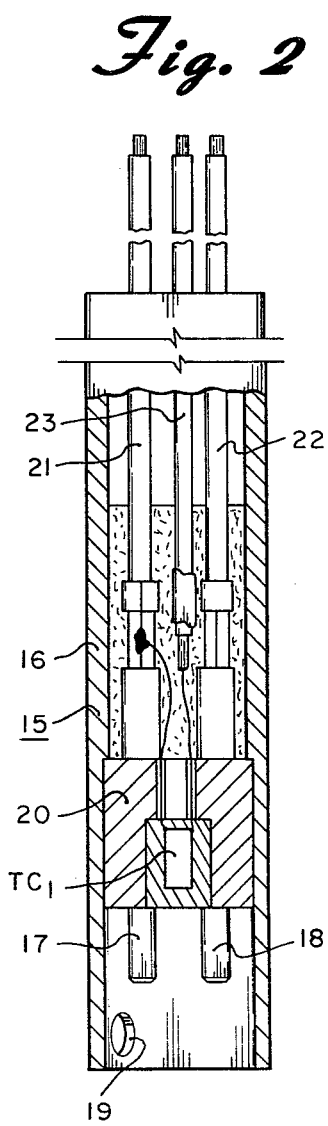
FIG. 2 is a sectional view of the probe assembly of the salts monitor of FIG. 1.

The salts monitoring apparatus of the present invention including its housing and probe assembly is shown in FIGS. 1 and 2 of the drawings. The salts monitoring meter 10 includes a two-part housing 11 and 12 into which the electronics are packaged. The housing is portable and short in length, such as 20 centimeters. In the upper portion of the housing, there is mounted a meter movement 13 which includes face indicia 14 thereon which is calibrated in terms of either color coded ranges or numerical indicia in reference to the salt levels to be found in the body. The salts monitoring paratus 10 also includes a conductivity probe assembly 15 secured at its upper end in the housing and depending below the housing.

The details of the conductivity probe assembly 15 are shown in FIG. 2 of the drawings. The housing 16 for the probe assembly 15 is of a suitable plastic material such as polyvinyl chloride or other polymeric plastic which is rigid and inert with respect to urine. Two stainless steel electrodes 17 and 18 are positioned in the lower end of the housing 16 and recessed back from the end of the housing 16 a short distance to place the electrodes 17 and 18 into a recessed pocket to provide a controlled monitoring environment. With a small device of the type disclosed herein, linearity of readings requires a control on the exposed length and spacing of electrodes 17, 18. These electrodes are preferably $\frac{1}{4}$ inch on center and have an exposed length of $\frac{1}{4}$ inch. A temperature sensing device $TC_1$ is secured in place in the epoxy plug 20 and adjacent the electrodes 17 and 18.

A lead 21 is connected to electrode 17 and extends from the probe assembly to the electronics within the housings 11 and 12. In a like manner, a lead 22 is connected to electrode 18 and extends into the housings. The temperature sensing device $TC_1$ has one of its leads connected to electrode 17 and its other lead connected to lead 23 which likewise extends from the probe assembly to the electronics positioned within the housing portions 11 and 12 all as shown in FIG. 2 of the drawings.

Figure 3:
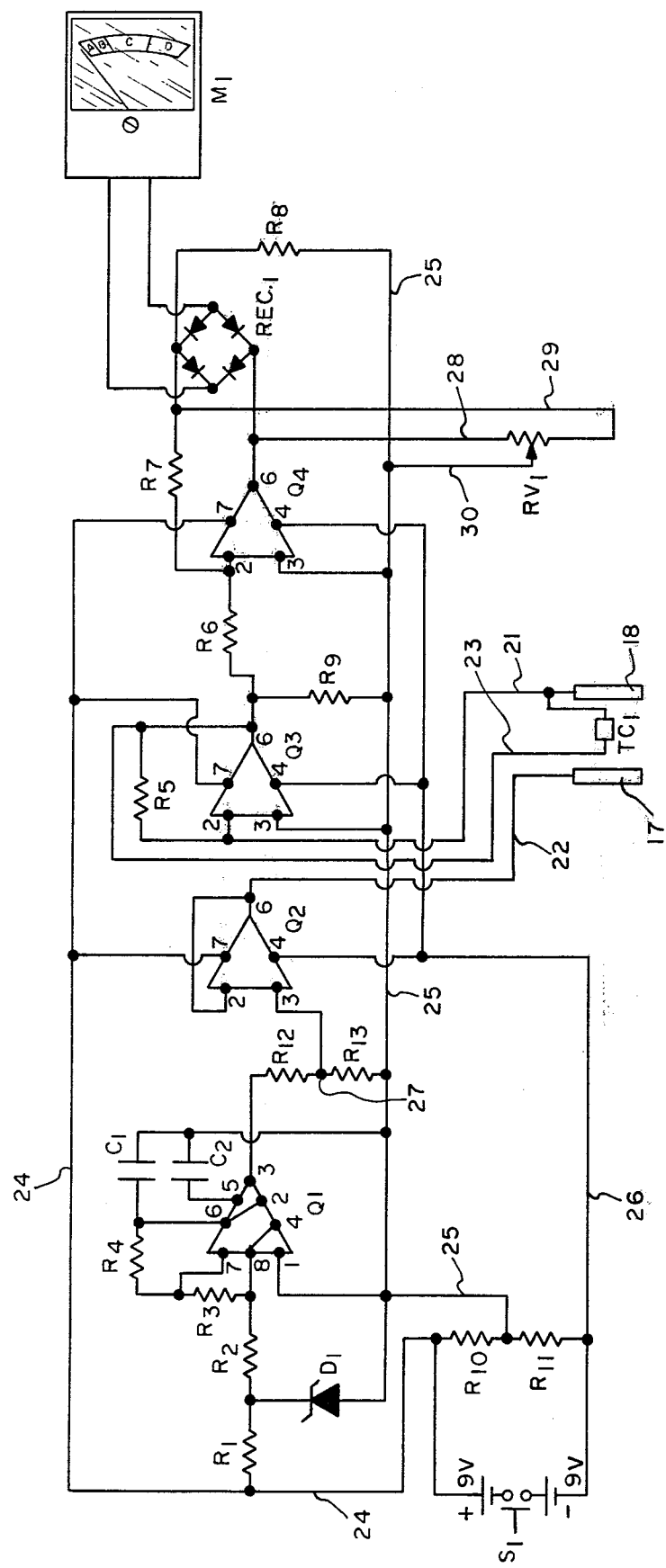
FIG. 3 is a schematic diagram of the circuitry of the salts monitoring apparatus of the present invention.

The electronic circuitry of the salts monitoring apparatus of the present invention is shown in FIG. 3 of the drawings. The power supply for the circuitry is provided by an 18 volt storage battery source which, in the embodiment shown in FIG. 3, consists of two 9 volt batteries connected in series through an energizing switch $S_1$. The two 9 volt batteries operate through a voltage divider network consisting of two resistors $R_{10}$ and $R_{11}$.

The impedance of resistor $R_{10}$ is substantially greater than that of $R_{11}$. Thus, the power supply generates a first voltage level upon line 24 which is substantially larger than the voltage level appearing on line 25 connected to the center point of the voltage divider all in respect to the ground line 26.

The salts monitoring circuitry of the present invention includes reference voltage generating means including IC circuit devices $Q_1$ and $Q_2$. $Q_1$ is a square wave generator or timer commercially available and designated as NE555 timer. The pin designation shown for $Q_1$ are those designated by the component manufacturer.

A Zener diode $D_1$ operating through a current limiting resistor $R_1$ is interconnected between the first and second voltage level lines 24 and 25 to provide a controlled voltage level input through resistor $R_2$ to the control voltage input to IC device $Q_1$ at pin 8. A jumper is applied across pins 6 and 2 to provide free running configuration for the timer. Likewise, the remainder of the pin connections, as shown in FIG. 3, are made utilizing resistors $R_3$ and $R_4$ as well as capacitors $C_1$ and $C_2$ to provide oscillator timing of approximately 80 microseconds.

The output of the timer $Q_1$ from pin 3 is applied across a voltage divider consisting of resistors $R_{12}$ and $R_{13}$ which are tied to line 25 which is the second voltage level. Resistor $R_{12}$ is substantially large relative to resistor $R_{13}$. Thus, the AC wave form appearing at the output of $Q_1$ when viewed at the midpoint of the voltage divider between resistors $R_{12}$ and $R_{13}$ is substantially reduced in magnitude and is positioned slightly above the second voltage level from the power supply apparent on line 25. However, this output wave form at the center point of the voltage divider between $R_{12}$ and $R_{13}$ is set at a predetermined level above the ground line 26 although its magnitude of wave form is substantially diminished.

The second alternating current signal of substantially reduced magnitude appearing at the center point 27 of the voltage divider formed by resistors $R_{12}$ and $R_{13}$ is applied as the non-inverting input to pin 3 of IC device $Q_2$. $Q_2$ is an operational amplifier available under commercial designation $\mu$ A 741. This IC device is an operational amplifier.

The power supply to integrated circuit device $Q_2$ is by means of the first voltage level on line 24 which provides the $V^+$ voltage at pin 7 whereas the $V^-$ connection from pin 4 is made to ground line 26. Thus, $Q_2$ is across the full voltage level between the first voltage level and ground of the power supply.

The output from $Q_2$ at pin 6 is applied directly back to the inverting input of the IC device at pin 2 without resistance. This configuration provides a voltage follower which provides a high input impedance and a low output impedance wherein the output voltage is of direct sign and magnitude to the input voltage. Accordingly, the output signal at pin 6 of IC device $Q_2$ will be identical to the input signal, i.e., slightly above the level upon line 25 but at a predetermined level above ground line 26 while also providing a low output impedance to thus provide the current necessary for operation of the remainder of the circuitry.

The output of pin 6 from $Q_2$ provides the final output from the reference voltage generating means consisting of $Q_1$ and $Q_2$. This output signal is applied to the voltage probe assembly which includes stainless steel electrodes 17 and 18. Specifically, the output signal from $Q_2$ is applied directly, by means of lead 22, to electrode 17.

Electrode 18 is connected, by means of lead 21, to the inverting input at pin 2 of an operational amplifier $Q_3$. The current flow from electrode 17 to 18 through the sample being monitored will be a function of the total dissolved ionizable salts. Thus, the current flow or signal appearing at the inverting input of $Q_3$, and thus the output of $Q_3$ will be a function of the total dissolved ionizable salts in the sample.

IC device $Q_3$ is the same operational amplifier as $Q_2$, i.e., $\mu$ A 741 C. This IC device is placed in circuit in the conventional operational amplifier configuration in that its $V^+$ input at pin 7 is applied to the first voltage level line 24 and its $V^-$ pin 4 interconnected to the ground line 26. Additionally, the output appearing at pin 6 is applied back to the inverting input at pin 2 by means of current limiting resistor R₅. Lastly, the inverting input at pin 3 is tied to a level above ground, in a conventional manner, by interconnection to the second voltage level line 25. In this configuration, IC device $Q_3$ operates in a normal operational amplifier manner with the inverting input signal at pin 2 being amplified at pin 6 as determined by the value of R₅.

Temperature compensating device $TC_1$ is interconnected into the feedback circuit by having one of its leads connected to lead 21 of electrode 18 which provides the inverting input to $Q_3$. The other lead of temperature sensing device $TC_1$ is connected in circuit by means of lead 23 to the output of $Q_3$ at pin 6. In this manner, a portion of the output from pin 6 is fed back through $TC_1$ to the inverting input of $Q_3$ at pin 2. The device $TC_1$ is chosen such that it will provide linear temperature compensation for the input to $Q_3$ to provide consistent readings with temperature variation of the sample being tested.

The output of $Q_3$ is applied across a voltage drop resistor R₉ which is connected to the second level voltage line 25. The signal developed across R₉ is applied, by means of voltage limiting resistor R₆, as the inverting input to a second operational amplifier $Q_4$ which is the same IC device as $Q_3$ and interconnected in the same configuration. Thus, the output from $Q_3$ is again inverted and further amplified by means of $Q_4$.

The feedback circuit for $Q_4$ is formed by means of a variable resistor $RV_1$ placed in circuit by means of leads 28 and 29 back through resistor R₇ to the inverting input of $Q_4$ at pin 2. The variable or adjustable terminal of variable resistor $RV_1$ is applied back through lead 30 to the second voltage level line 25. Adjustment of variable resistor $RV_1$, working through feedback resistor R₇ in the feedback circuit, and resistor R₈ placed in parallel with the feedback resistor R₇ and the second voltage level line 25 provides trimming of the feedback circuitry to $Q_4$ to provide calibration for the indicating circuitry as hereinafter described.

The output of IC device $Q_4$ provides one side of the input to a full wave rectifier device $REC_1$ which, in the embodiment shown in FIG. 3, is a four diode rectifier of the conventional configuration. The other input side to the rectifying device $REC_1$ is provided by means of resistor R₈ back through the second voltage level line 25. The output voltage of $Q_4$ will swing above and below the voltage level on voltage level line 25 inasmuch as the V₋ input to $Q_4$ is tied back to the ground line 26.

The output of rectifying device $REC_1$ is applied across a meter movement $M_1$. The full wave rectified square wave signal appearing across the output of $REC_1$ is proportional to and representative of the total dissolved ionizable salts in the urine sample being monitored. Appropriate trimming of variable resistor $RV_1$ will calibrate the meter movement as required for fine trimming of the system. The meter movement, as previously indicated, may include either direct readings of Microhmos or include color coded indicia to indicate various levels of acceptable or non-acceptable salt levels.

In a preferred embodiment, the component values and designations are as follows:

| | |
|---|---|
| R₁ | 680 |
| R₂ | 330 |
| R₃ | 2.7K |
| R₄ | 5.1K |
| R₅ | 2.7K |
| R₆ | 10K |
| R₇ | 47K |
| R₈ | 10K |
| R₉ | 10K |
| R₁₀ | 120K |
| R₁₁ | 1.6K |
| R₁₂ | 10K |
| R₁₃ | 51 |
| C₁ | .01UF |
| C₂ | .1UF |
| D₁ | 5.6 Zener |
| RV₁ | 10K |
| REC₁ | 1N914(f) |
| Q₁ | NE555 |
| Q₂–Q₄ | μA741C |
| M₁ | 0–300 AMP-DC |

As will be seen from the foregoing, the salts monitoring apparatus of the present invention provides a reliable and dependable as well as efficient yet economical circuitry for monitoring the quantity of total dissolved ionizable salts in an indiluted sample. Electrodes 17, 18 are stainless steel so as to be durable, never need replacing and are easily cleaned by immersion in water and then dried. The immersion depth of probe assembly 15 in the sample is small, such as ½ inch.

The present invention may be embodied in other specific forms without departing from the spirit or essential attributes thereof and, accordingly, reference should be made to the appended claims, rather than to the foregoing specification, as indicating the scope of the invention.

What is claimed is:

1. A small portable monitor usable by an unskilled person for measuring the quantity of total dissolved ionized salts in an undiluted sample comprising:

power supply means for providing in operation a first voltage level and a second and substantially lower voltage level with reference to the power supply ground;

reference voltage generating means including a first alternating current generating means across the first and second voltage levels and providing a first alternating current output cycling between the first and second voltage levels above ground;

a voltage divider having a first leg of relatively high impedance connected between the first alternating current output and a center point and a second leg of relatively low impedance connected between the center point and the second voltage level to provide a second alternating current output from the center point of the voltage divider of substantially reduced magnitude set a predetermined and controlled level above the second voltage level;

an operational amplifier connected into a voltage follower configuration wherein the second alternating current output provides the input to the operational amplifier and the first voltage level and the ground provide the power supply to the operational amplifier and wherein the output of the operational amplifier is the final output of the reference voltage generating means;

a conductivity sensing probe assembly including two spaced electrodes adapted to be submerged in an undiluted sample to be tested, said electrodes being made from a material which is not ionized by the undiluted sample;

amplifier means energized by the power supply means and having an input and output;

circuit means connecting one electrode of the probe assembly to the output of the operational amplifier and the other electrode to the input of the amplifier means thereby providing an input level to the amplifier as a function of the quantity of the total dissolved ionized salts in the sample;

indicator means responsive to the output of the amplifier means providing an indication having a predetermined relationship to the quantity of the total dissolved ionized salts in the sample.

2. The salts monitor of claim 1 further including a Zener diode between the first and second voltage levels to provide a controlled voltage input to the first alternating current generating means.

3. The salts monitor of claim 1 wherein the amplifier means includes two operational amplifiers connected in series.

4. The salts monitor of claim 1 wherein the indicator means includes bridge means and a meter movement.

5. The salts monitor of claim 1 wherein the probe assembly further includes temperature sensing means to vary the input level to the amplifier in a slope and direction to compensate for temperature variation of the temperature of the sample being tested.

* * * * *